United States Patent [19]

Waknine

[11] Patent Number: 4,839,401
[45] Date of Patent: Jun. 13, 1989

[54] LIGHT CURABLE DENTAL PIT AND FISSURE SEALANT

[75] Inventor: Samuel Waknine, Wallingford, Conn.

[73] Assignee: Jeneric/Pentron, Inc., Wallingford, Conn.

[21] Appl. No.: 913,617

[22] Filed: Sep. 30, 1986

Related U.S. Application Data

[63] Continuation-in-part of Ser. No. 754,236, Jul. 12, 1985, abandoned.

[51] Int. Cl.$^4$ .......................... C08F 2/50; C08F 20/30; C08F 20/34; C08K 5/47
[52] U.S. Cl. .......................... 522/14; 522/16; 522/21; 522/28; 522/75; 522/81; 522/83; 522/103; 522/908; 523/116
[58] Field of Search .................................... 522/28, 14

[56] References Cited

U.S. PATENT DOCUMENTS

| | | | |
|---|---|---|---|
| 4,407,984 | 10/1983 | Ratcliffe | 522/14 |
| 4,457,818 | 7/1984 | Denyer | 522/28 |
| 4,459,193 | 7/1984 | Ratcliffe | 522/28 |
| 4,479,782 | 10/1984 | Orlowski | 522/14 |

OTHER PUBLICATIONS

Roffey, "Photopolymerization of Surface Coatings", John Wiley & Sons, 1982, pp. 113, 152, 283.

*Primary Examiner*—John C. Bleutge
*Assistant Examiner*—Arthur H. Koeckert
*Attorney, Agent, or Firm*—Kramer, Brufsky & Cifelli

[57] ABSTRACT

A light curable pit and fissure sealant composition comprises 2,2-propane-bis [3-(4-phenoxy)-1,2-dihydroxypropane-1- methacrylate] and triethylene glycol dimethacrylate in a 55:45 weight ratio, a polymerization initiator, titanium dioxide as an opaquing agent, and DEA-EMA of at least 95 percent purity as the polymerization accelerator. Optionally, up to 50% filler can be used.

15 Claims, No Drawings

LIGHT CURABLE DENTAL PIT AND FISSURE SEALANT

CROSS-REFERENCE TO RELATED APPLICATION

This is a continuation-in-part of application Ser. No. 754,236 filed on July 12, 1985, now abandoned.

BACKGROUND OF THE INVENTION

This invention relates to compositions and methods for sealing pits and fissures in tooth enamel surfaces. More particularly, it relates to visible light curable sealant compositions.

Dental surface imperfections such as pits and fissures can harbor microorganisms which, on proliferation, cause the formation of caries. These imperfections are particularly troublesome in deciduous teeth and have historically been the source of great discomfort for children. Ordinary dental hygienic methods such as toothbrushing and professional prophylaxis are quite ineffective against these imperfections since such pits and fissures are typically too narrow to permit contact by bristles or prophylaxis instruments.

In order to avoid the problems caused by microorganism growth and adhesion in dental pits and fissures, the general practice now is to seal these imperfections in order to eliminate the sites for proliferation of such microorganisms. The generally used pit and fissure sealants contain polymerizable resins such as the polymerizable acrylic resin system for use in dentistry described in U.S. Pat. No. 3,066,112. These polymerizable resins are used without filler in order to provide a sealant of sufficiently low viscosity to flow into the pits and fissures so as to assure complete sealing and good adhesion to the surrounding tooth surface.

The polymereizable resin systems usable as pit and fissure sealants can include many resins within the wide range of acrylic monomers and the diluent monomers currently used in restorative dentistry. The resinous compositions also include the necessary polymerization initiators and accelerators and the optional (but preferable) inhibitors and ultraviolet absorbers.

Although excellent sealing and adhesion can be obtained by the use of various polymerizable acrylic resin systems, such resin systems are generally either transparent or translucent and consequently it is difficult for the dentist to discern whether the sealant has been properly placed. Thus, it is often quite difficult to determine whether the pits and fissures are completely sealed, whether some pits and fissures have remained unsealed or, conversely, whether too much sealant has been used. Furthermore, subsequent examinations by the dentist to determine whether sealant has become worn or dislodged are rendered difficult or uncertain because of the difficulty in ascertaining the presence or absence of such transparent or translucent sealants.

The addition of a pigment to polymerizable resin sealant composition provides an easily discernable composition which avoids the problems encountered by transparent or translucent dental sealants. However, such pigments tend to settle out of the sealant composition upon standing. Therefore, the sealant composition containing pigment must be stirred thoroughly prior to each use or, alternatively, the pigment cannot be added until the sealant composition is ready for use. In U.S. Pat. No. 4,150,012, there is disclosed a two-part pit and fissure sealant composition containing an opaquing filler material and a hydrophobic suspending agent.

Despite recent improvements as far as opacity is concerned, improvements in the physical characteristics of the sealants themselves are desirable. In particular, it is desirable to develop suitable readily discernable pit and fissure sealants which exhibit improved surface hardness versus depth of cure and ultimate degree of polymerization. In addition, it is desirable to provide sealants which exhibit improved diametral tensile strength sufficient to avoid premature edgewise chip fracture and which exhibit improved retention. In addition, sealants exhibiting these properties coupled with the convenience of a visible light curing technique would be particularly desirable.

SUMMARY OF THE INVENTION

This invention provides a visible light curable pit and fissure sealing composition which composition comprises from about 40 to about 70 weight percent of the condensation product of bisphenol A and glycidyl methacrylate (BIS-GMA), from about 30 to 60 weight percent of triethylene glycol dimethacrylate (TEGDM), from about 0.05 to about 0.5 weight percent of titanium dioxide powder, from about 0.6 to about 1.6 percent of a UV-absorber, from about 0.1 to about 0.4 percent of diethylaminoethylmethacrylate (DEAEMA) of at least 95 percent purity and from about 0.05 to about 0.30 weight percent of a polymerization initiator. The weight ratio of BIS-GMA to TEGDM is about 30-80:70-20, most preferably about 55:45. Optionally, up to 50 weight percent $SiO_2$ may be included as filler. Preferably, about 4 wt % colloidal fumed silica is used in the practice of this invention.

Pit and fissure sealant compositions according to this invention are quite stable, have excellent physical properties and adhere very well to tooth structure. The use of high-purity diethylaminoethylmethacrylate (DEAEMA) as the polymerization accelerator is responsible for the improved physical properties.

DETAILED DISCLOSURE OF THE INVENTION

The organic methacrylic phenolic epoxy monomer usable in the compositions of this invention is the condensation product of bisphenol A and glycidyl methacrylate, generally abbreviated to BIS-GMA, which chemically is 2,2-propane-bis[3-(4-phenoxy)-1,2-dihydroxy-propane-1-methacrylate]. Because of its excellent combination of physical properties, i.e., diametral tensile strength, water sorption, index of refraction, shrinkage, lack of toxicity, and biocompatability, BIS-GMA is the most frequently used monomer in methacrylic phenolic epoxy resin-based dental compositions. However, because of its extreme viscosity at room temperature, other methacrylate monomers are used as diluents. In the practice of this invention, the diluent monomer is triethylene glycol dimethacrylate, commonly abbreviated to TEGDM. It has been found, for the purposes of the sealant compositions of this invention, that a BIS-GMA to TEGDM ratio of about 30–80 percent to 70–20 percent by weight, most preferably 55 percent to 45 percent by weight, produces the best results, from a rheological and mechanical standpoint.

As the opaquing agent, titanium dioxide powder, a well known pigment, is used. The particle size of titanium dioxide should range between about 0.1 to 2.0 microns. The opaquing agent should be present in sufficient amount to cause the resinous material to be easily visible both when it is applied as a free flowing liquid and, after application, in order that the dentist be able to discern the presence of the sealant. With a particle size in the range of from about 0.2 to about 0.7 microns, it has been found that from about 0.05 percent to about 0.50 percent, preferably about 0.1 percent, by weight of titanium dioxide, based on the weight of polymerizable resin, is sufficient for opaquing purposes. Amounts of titanium dioxide of up to about 2 percent, however, can be used in the practice of this invention. The resinous composition is a visible light curable composition and thus requires the presence of a polymerization initiator.

As polymerization initiators, visible light initiators such as benzil and 2,3-d-boranedione, commonly referred to as dl-camphoroquinone, preferably of at least .99% purity, can be employed. Either one of these initiators can be used singly, or both may be used in combination. It has been found that from about 0.05 to about 0.30 weight percent, preferably from about 0.1 to about 0.3 weight percent of d,1-camphoroquinone is sufficient.

The compositions of this invention include diethylaminoethylmethacrylate (commonly referred to as DEA-EMA) as a polymerization accelerator. In addition, it is considered preferable to employ either 50–100 ppm phenothiazine (PTZ), preferably 100 ppm PTZ, or 800–1200 ppm methyl ether hydroquinone (MEHQ), preferably 1000 ppm MEHQ. The phenothiazine is present in the monomer to prevent polymerization which results in gelation. Numerous tertiary amines, such as diethylaminoethylacrylate (DEA-EA) and dimethylaminoethylmethacrylate, (DMA-EMA) heretofore have been used as polymerization accelerators in the past. Although DMA-EMA is the customary tertiary amine utilized in virtually all current commercial visible light cure resin formulations, it has surprisingly been found that in the formulations, it has surprisingly been found that in the sealant compositions of this invention, DEA-EMA of at least 95 percent, and preferably of at least 98.5 percent, purity, provides optimum physical properties. Use of this high-purity DEA-EMA rather than, for example, DEA-EMA of lower purity or DMA-EMA, provides a sealant with significantly improved diametral tensile strength, greater hardness and excellent color stability.

In order to provide a sealant solution with satisfactory handling characteristics for some applications, it is necessary to add a hydrophobic suspension agent to the composition. The suspension agent contemplated here is hydrophobic colloidal fumed silica, which additionally improves the wear characteristics and minimizes water uptake by the sealant. The fumed silica is of submicron particle size, generally from about 0.01 to about 0.05 microns. The colloidal fumed silica may be used alone in amounts from about 0 to 7 wt. %.

The optimum weight percent of colloidal fumed silica to obtain optimal mechanical properties yet maintain proper viscosity to enable flow into pit or fissure depths was found to be about 4%. Beyond this amount, the colloid tends to agglomerate, form stress concentrated areas that hinder strength characteristics, scatter light leading to improper depth of cure and overthicken resin to the point where it will not permeate to the put or fissure floor in the molar occlusal surface of the tooth. combination with one or more of barium boro-silicate, strontium boro-silicate, lithium alumina-silicate and fused quartz. This combination may be used in quantities up to 50 weight percent and are added in quantities such that as close to proper flow as possible is maintained. When using the above-mentioned combinations, it is preferred that up to 4 weight percent colloidal fumed silica is used with up to 46% weight percent of the latter fillers. In the case where a minimum of 50 weight percent of combined filler is desired, the use of 2 to 3 weight percent colloidal fumed silica is preferred.

The sealant compositions of this invention can also include an ultraviolet stabilizer, such as for example, the benzotriazole derivative sold under the trademark TINUVIN P by Ciba-Geigy Corporation, Ardsley, New York or the benzophenones UV-9 and UV-5411 of American Cyanamid Company, Wayne, New Jersey. From about 0.6 to about 1.6 weight percent can be used preferably from about 0.5 to about 1.5 weight percent of benzotriazole UV-absorber.

Typical unfilled sealants according to this invention have the following approximate compositions:
52.5—54 weight percent BIS-GMA
43—44 weight percent of TEGDM
0.05—0.50 weight percent titanium dioxide
0.6—1.6 weight percent of UV-absorber
0.1—0.4 weight percent of DEA-EMA (95+% purity) containing 100 ppm PTZ
0.5—0.30 weight percent of camphoroquinone (99% purity)
0.05—0.30 weight percent of camphoroquinone (99% purity)

The weight ratio of BIS-GMA to TEGDM is about 55:45.

Typical partially filled sealant compositions contain, in addition to the above-mentioned ingredients, 0–7 weight percent of colloidal fumed silica.

Typical low-to-medium filled sealant compositions contain, in addition to the ingredients of the unfilled sealant, up to about 4 weight percent of colloidal fumed silica and 26–30 weight percent of one or more of barium boro-silicate, strontium boro-silicate, lithium alumina-silicate and fused quartz.

Finally, typical medium-to-highly filled sealants according to this invention contain, in addition to the ingredients recited in the unfilled composition, 2–3 weight percent colloidal fumed silica and up to a total 50 weight percent of one or more of barium boro-silicate, strontium boro-silicate, lithium alumina-silicate and fused quartz.

The visible light curable pit and fissure sealant compositions of this invention can be prepared by mixing together the various ingredients in their respective proportions. The order of mixing is not considered important. The composition is then applied to a properly prepared tooth enamel surface, in particular, a surface etched with, for example, 37% orthophosphoric acid gel. After application, polymerization is effected by exposure to a visible light source, for example a 150 watt halogen light source or any visible light source which is capable of generating visible light within wavelengths ranging from about 250 to about 750 nanometers, perferably from about 450 to 500 nanometers, and most preferably from about 468 to about 480 nanometers, for about 20 seconds.

This invention will be better understood by reference to the following examples, which are here included for illustrative purposes only and are not to be construed as limitations. Unless otherwise stated, all percentages and parts are by weight.

EXAMPLE 1

A pit and fissure sealant composition is prepared by mixing together the following ingredient in the proportions stated:
BIS-GMA—53.14 parts
TEGDM—43.38 parts
Titanium Dioxide Powder—0.097 parts
TINUVIN P UV-absorber—0.97 parts
dl-camphoroquinone—0.1594 parts (99% purity)
DEA-EMA—0.2222 parts (98.5% purity)
Colloidal Fumed Silica—3.9714 parts This composition, when applied to a properly prepared dental enamel surface and exposed to visible light for 20 seconds, provides effective sealing of pits and fissures. The sealant, being opaque, is readily discernable. Furthermore, the sealant, when in place, has, owing to the use of high purity DEA-EMA, excellent physical properties which provide improved durability.

EXAMPLE 2

A pit and fissure sealant composition is prepared by mixing together the following ingredients in the proportions stated:
BIS-GMA 55 parts
TEGDM 45 parts
Benzotrizole 1 part
d,1-camphoroquinone 0.1650 parts
DEA-EMA w/100 ppm PTZ 0.2300 parts

EXAMPLE 3

To demonstrate the surprising effect that DEA-EMA has on the diametral tensile strength (DTS) of the sealant composition prepared as described hereinabove, several samples of the composite resin of the present invention were prepared in identical manner except that the tertiary amine used was different.

DTS samples were prepared by curing the various samples of composite resin for 40 seconds with an OPTILUX visible light source available from Demetron Corporation, Danbury, Connecticut. The samples were cured in a 6 mm. diameter ×3 mm stainless steel split cylindrical mold, set on 25 ×75 mm glass microslides, condensed with a stainless steel spatula and covered with a glass cover micro slip 25 ×25 mm. The cured samples were immersed within 2 minutes of curing into a 37° C. +0.1° C., hour intervals. The samples were then subjected to diametral compression on an Instron machine at 1"/minute chart speed and 0.02"/minute cross head speed and then the pounds of load applied to cause fracture of the specimens were noted and employed to calculate the DTS. (DTS=2P/ dl wherein P=load, d=specimen diameter and l=length of specimen). The average of 6 measurements are summarized below.

As can be seen from the data below, a surprising and significant increase in DTS is achieved by employing DEA-EMA in the sealant composition. A statistically significant difference is apparent between the three tertiary amine types for the combined 15 minute and 24 hour means at 99.99% confidence level or better in accordance with a two way analysis of the variants of aging time versus amine type. It shoudl also be noted that the sealant composition containing DEA-EMA strengthens upon aging due to an enhanced continued polymerization.

|  | DEA-EMA | DMA-EMA | *DMA-EA |
|---|---|---|---|
| 15 min. D.T.S. PSI | 3439 | 2332 | 3021 |
| 24 hrs. D.T.S. PSI | 3839 | 2473 | 3180 |

*The DMA-EA contains 1000 ppm MEHQ (methyl etherhydroquinone) as the inhibitor rather than PTZ.

EXAMPLE 4

The immediate Barcol hardness/depth at 3 millimeter depth for top/bottom was determined for each of the sealant compositions in Example 5.

A GYZJ 935 Barcol Hardness Barber Colman portable impressor was employed. Samples of each material were cured for 40 seconds using a OPTILUX visible light source in a 3 mm depth stainless steel mold of 10 mm. diameter set on 25 ×75 mm microglass slides and covered with 25 ×25 mm. cover glass. The average of 5 Barcol hardness measurements for each side top/bottom were noted. The results are summarized below.

| AVG. surface Barcol Hardness vs. depth of cure | DEA-EMA | DMA-EMA | DMA-EA |
|---|---|---|---|
| 3 mm | | | |
| Top | 80.8 | 76.2 | 76.2 |
| Bottom | 68.2 | 59.0 | 58.8 |

From the foregoing, it can readily be seen that the composite of the present invention shows the greater top/bottom Barcol hardness and depth of cure at 3mm. A statistically significant difference is apparent between the DEA-EMA and the latter two amines for the 3 mm means at 99.99% confidence level or better in accordance with a two way analysis of variants of depth of cure versus amine type.

What is claimed is:

1. A visible light curable dental composition for filling and sealing pits and fissures which composition comprises from about 40 to about 70 weight percent of the condensation product of bisphenol A and glycidyl methacrylate (BIS-GMA), from about 30 to 60 weight percent of triethylene glycol dimethacrylate (TEGDM), up to about 2 weight percent of titanium dioxide powder, from about 0.6 to about 1.6 percent of a UV-absorber, from about 0.1 to about 0.4 percent of diethylaminoethylmethacrylate (DEA-EMA) of at least 95 percent purity and from about 0.05 to about 0.30 weight percent of a polymerization initiator, the weight ratio of BIS-GMA to TEGDM being about 30-80:-70-20.

2. A composition according to claim 1 in which the weight ratio of BIS-GMA to TEGDM is about 55.45.

3. A composition according to claim 1 further comprising diethylaminoethylmethacrylate containing 50-100 ppm phenothiazine.

4. A composition according to claim 3 wherein the diethylaminoethylmethacrylate contains 100 ppm phenothiazine.

5. A composition according to claim 1 further comprising diethylaminoethylmethacrylate containing 800-1200 ppm methyl ether hydroquinone.

6. A composition according to claim 5 wherein the diethylaminoethylmethacrylate contains 1000 ppm methyl ether hydroquinone.

7. A composition according to claim 1 further comprising up to about 7 weight percent of colloidal fumed silica.

8. A composition according to claim 1 further comprising up to 4 weight percent of colloidal fumed silica and up to 46 weight percent of at least one of barium borosilicate, strontium boro-silicate, lithium aluminasilicate and fused quartz.

9. A composition according to claim 1 further comprising 2-3 weight percent of colloidal fumed silica and up to a total 50 weight percent of at least one of barium borosilicate, strontium boro-silicate, lithium aluminasilicate and fused quartz.

10. A composition according to claim 1 in which the polymerization initiator is selected from the group consisting of benzil and dl-camphoroquinone.

11. A composition according to claim 5 which additionally comprises from about 0.5 to about 1.5 weight percent of benzotriazole UV-absorber and from about 0.1 to about 0.3 weight percent of dl-camphoroquinone.

12. A composition according to claim 1 in which the particle size of the titanium dioxide powder ranges from about 0.2 to about 0.7 microns.

13. A composition according to claim 7 in which the titanium dioxide is present in an amount from about 0.05 to about 0.5 weight percent.

14. A composition according to claim 7 in which the titanium dioxide is present in an amount of about 0.1 weight percent.

15. A composition according to claim 1 in which the DEA-EMA is at least about 98.5 percent pure.

* * * * *

UNITED STATES PATENT AND TRADEMARK OFFICE
CERTIFICATE OF CORRECTION

PATENT NO. : 4,839,401

DATED : June 13, 1989

INVENTOR(S) : Samuel Waknine

It is certified that error appears in the above-identified patent and that said Letters Patent is hereby corrected as shown below:

At Column 3, line 14, "2,3-d-boranedione" should read
-- 2,3-d-bornandione -- .

At Column 3, lines 36-37, "it has surprisingly been found that in the formulations" should be deleted.

At Column 3, line 63, "put" should read -- pit --.

At Column 4, line 12, delete "or the benzophenones UV-9 and UV-5411 of" and insert in lieu thereof, -- , the benzophenone UV-9 or the benzotriazole UV-5411, both available from -- .

At Column 4, lines 25-26, delete "0.5-0.30 weight percent of camphoroquinine (99% purity).

At Column 5, line 63, "variants" should read -- variance -- .

At Column 5, line 65, "shoudl", should read
-- should -- .

UNITED STATES PATENT AND TRADEMARK OFFICE
CERTIFICATE OF CORRECTION

PATENT NO. : 4,839,401

DATED : June 13, 1989

INVENTOR(S) : Samuel Waknine

It is certified that error appears in the above-identified patent and that said Letters Patent is hereby corrected as shown below:

At Column 6, line 40, "variants" should read -- variance --.

Signed and Sealed this

Twenty-first Day of August, 1990

Attest:

HARRY F. MANBECK, JR.

*Attesting Officer*    *Commissioner of Patents and Trademarks*